(12) United States Patent
Biederman et al.

(10) Patent No.: US 8,764,185 B1
(45) Date of Patent: Jul. 1, 2014

(54) DEVICES AND METHODS FOR A CONTACT LENS WITH AN INWARD FACING LIGHT SOURCE

(71) Applicant: Google Inc., Mountain View, CA (US)

(72) Inventors: William James Biederman, Fox Island, WA (US); Brian Otis, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/028,036

(22) Filed: Sep. 16, 2013

Related U.S. Application Data

(63) Continuation of application No. 13/931,411, filed on Jun. 28, 2013.

(51) Int. Cl.
*G02C 7/04* (2006.01)
(52) U.S. Cl.
USPC .................................................. 351/159.02
(58) Field of Classification Search
USPC ....... 351/160 R–165, 177, 159.02; 345/8, 30, 345/31, 87, 168, 905; 709/203; 715/277; 382/24
See application file for complete search history.

(56) References Cited

U.S. PATENT DOCUMENTS

| | | | |
|---|---|---|---|
| 5,297,554 A | 3/1994 | Glynn et al. | |
| 5,682,210 A | 10/1997 | Weirich | |
| 8,096,654 B2 | 1/2012 | Amirparviz et al. | |
| 8,446,341 B2 * | 5/2013 | Amirparviz et al. | 345/7 |
| 2009/0189974 A1 | 7/2009 | Deering | |
| 2010/0001926 A1 | 1/2010 | Amirparviz et al. | |
| 2010/0103368 A1 | 4/2010 | Amirparviz et al. | |
| 2012/0199995 A1 | 8/2012 | Pugh et al. | |
| 2012/0245444 A1 | 9/2012 | Otis et al. | |

FOREIGN PATENT DOCUMENTS

| | | |
|---|---|---|
| JP | 8154897 A | 6/1996 |
| WO | 2004015460 A2 | 2/2004 |
| WO | 2011094758 A2 | 8/2011 |

OTHER PUBLICATIONS

Babak A. Parviz, "For Your Eye Only", IEEE Spectrum, Sep. 2009.
Lingley et al., "A single-pixel wireless contact lens display", Journal of Micromechanics and Mocroengineering, 2011.
Mike Flacy, "Researchers Develop LCD Contact Lens that Display Your Text Messages", Digital Trends, Dec. 8, 2012.

* cited by examiner

*Primary Examiner* — Hung Dang
(74) *Attorney, Agent, or Firm* — McDonnell Boehnen Hulbert & Berghoff LLP

(57) ABSTRACT

An eye-mountable device can include a transparent material and a substrate at least partially embedded in the transparent material. The transparent material can have a concave surface and a convex surface, with the concave surface configured to removably mount the eye-mountable device on a corneal surface overlaying a pupil. A light source can be disposed on the substrate and configured to emit light through the concave surface and towards the corneal surface such that the emitted light is viewable through the pupil. The light source can be controlled by circuitry disposed on the substrate. The circuitry can be configured to modulate the light emitted by the light source to provide modulated light.

16 Claims, 11 Drawing Sheets

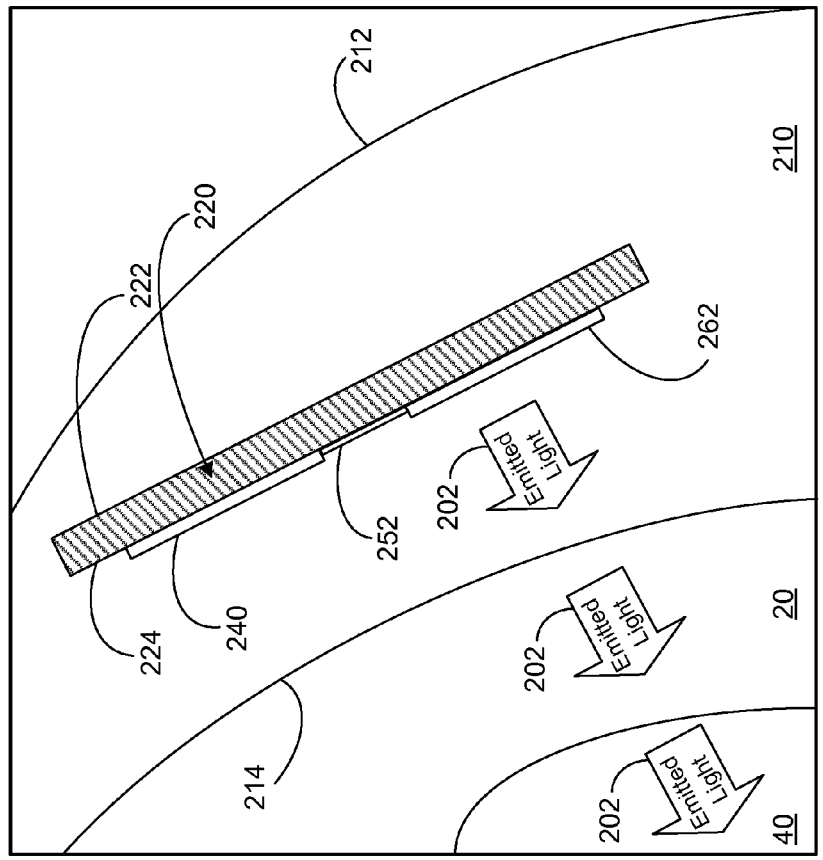
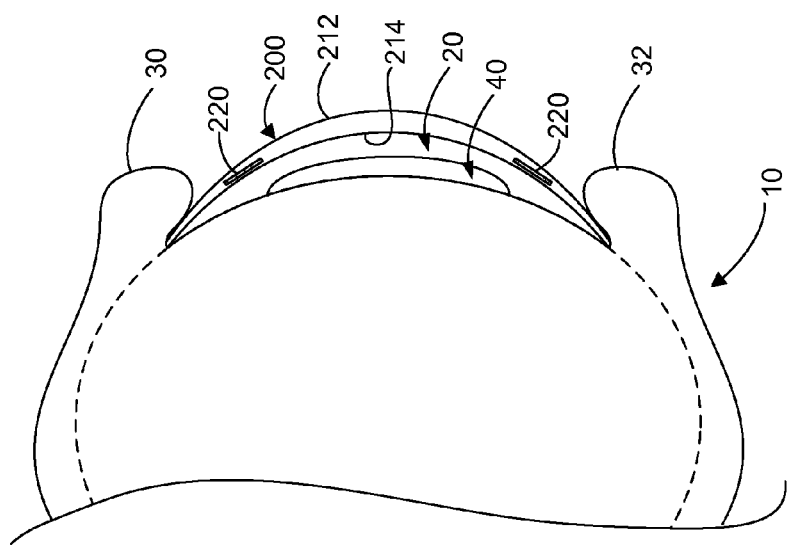

DEVICES AND METHODS FOR A CONTACT LENS WITH AN INWARD FACING LIGHT SOURCE

CROSS REFERENCE TO RELATED APPLICATIONS

The present application is a continuation of U.S. patent application Ser. No. 13/931,411, filed Jun. 28, 2013, which is currently pending. The entire disclosure contents of this application are herewith incorporated by reference into the present application.

BACKGROUND

Unless otherwise indicated herein, the materials described in this section are not prior art to the claims in this application and are not admitted to be prior art by inclusion in this section.

A contact lens device can include a sensor for measuring an analyte, such as glucose, in a tear film. The sensor can be an electrochemical sensor that includes a working electrode and a counter and/or reference electrode. An electrochemical reaction involving the analyte can transfer electrons to or from the working electrode so as to generate a current related to the concentration of the analyte. In some instances, a reagent can be located proximate to the working electrode to facilitate a selective, electrochemical reaction with the analyte.

A contact lens device can also communicate sensor readings to an external reader. For example, the contact lens can include an antenna that is configured to receive radio frequency radiation from the external reader and produce a backscatter signal based on a sensor reading.

SUMMARY

In one example, an eye-mountable device is provided that comprises a transparent material having a concave surface and a convex surface. The concave surface can be configured to be removably mounted over a corneal surface overlaying a pupil and the convex surface can be configured to be compatible with eyelid motion when the concave surface is so mounted. The device also comprises a substrate at least partially embedded in the transparent material. The device also comprises a light source disposed on the substrate. The light source can be configured to emit light that is viewable through the pupil when the concave surface is mounted on the corneal surface. The device also comprises circuitry disposed on the substrate. The circuitry can be configured to modulate the light emitted by the light source to provide modulated light.

In another example, a method performed by an eye-mountable device is provided. The method comprises mounting the eye-mountable device on a corneal surface such that the eye-mountable device overlays a pupil. The eye-mountable device can include a transparent material having a concave surface and a convex surface. The concave surface can be configured to be removably mounted on the corneal surface. The convex surface can be configured to be compatible with eyelid motion when the concave surface is so mounted. The method further comprises modulating light emitted by a light source included in the eye-mountable device. The light source can be disposed on a substrate that is at least partially embedded in the transparent material. The method further comprises emitting the modulated light through the concave surface of the eye-mountable device mounted on the corneal surface, such that the modulated light is viewable through the pupil.

In another example, a method performed by a computing device is provided. The method comprises transmitting, by the computing device, data to an eye-mountable device. The eye-mountable device can include a transparent material having a concave surface, a convex surface, and a substrate at least partially embedded in the transparent material. The concave surface can be configured to be removably mounted on a corneal surface overlaying a pupil. The convex surface can be configured to be compatible with eyelid motion when the concave surface is so mounted. The eye-mountable device can include a light source disposed on the substrate. The light source can be configured to emit light that is viewable through the pupil when the concave surface is so mounted. The eye-mountable device can include circuitry disposed on the substrate. The circuitry can be configured to control the light source. The method further comprises transmitting, by the computing device, instructions to the eye-mountable device. The instructions can be configured to cause the circuitry to modulate the light emitted by the light source based on the data to provide modulated light.

These as well as other aspects, advantages, and alternatives, will become apparent to those of ordinary skill in the art by reading the following detailed description, with reference where appropriate to the accompanying figures.

BRIEF DESCRIPTION OF THE FIGURES

FIG. 2C is a side cross-section view of the example eye-mountable device shown in FIGS. 2A and 2B while mounted to a corneal surface of an eye.

FIG. 2D is a close-in side cross-section view enhanced to show the substrate embedded in the transparent material, the light source, and the emitted light in the example eye-mountable device when mounted as shown in FIG. 2C.

DETAILED DESCRIPTION

Figure 1:
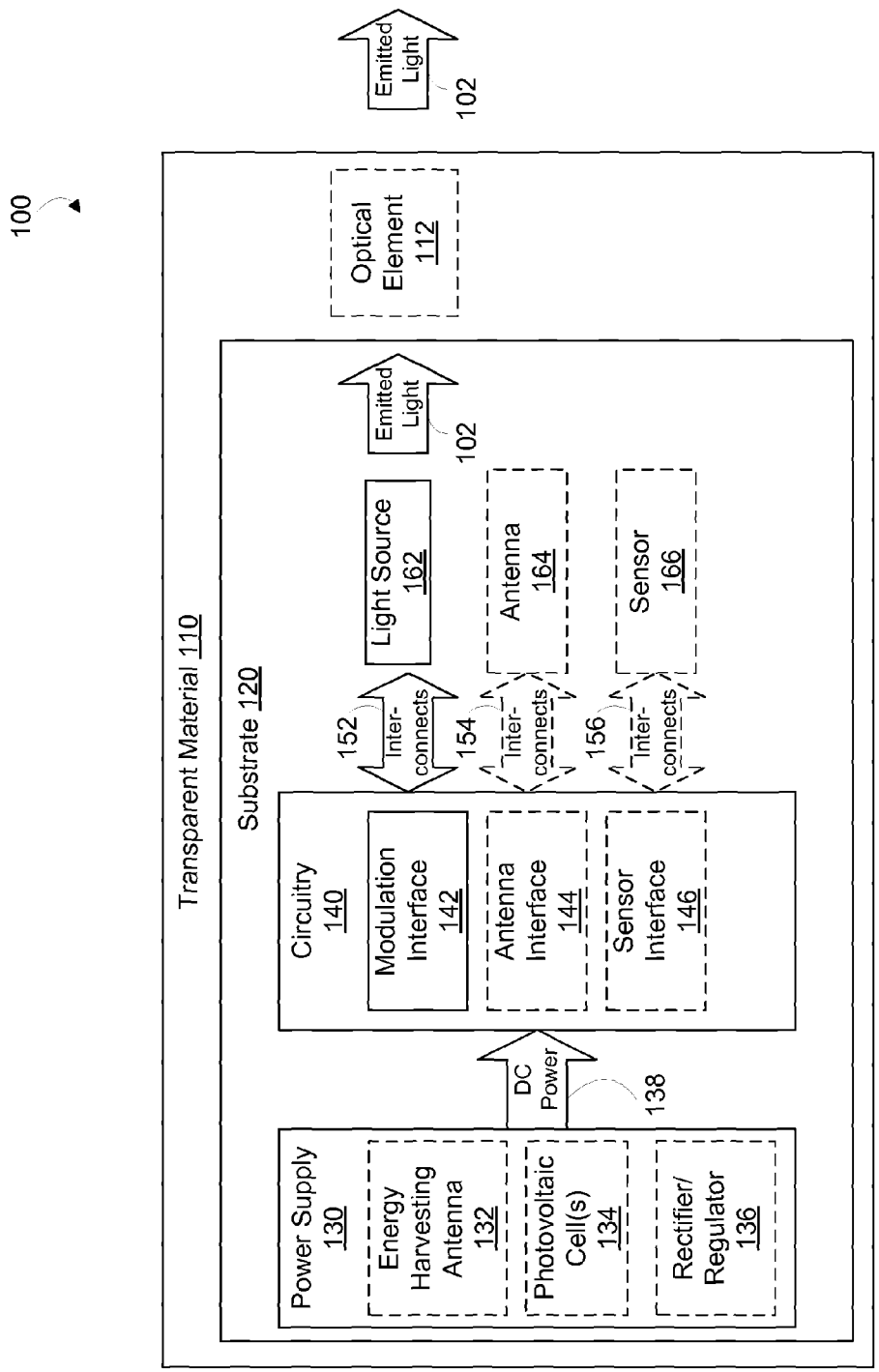
FIG. 1 is a block diagram of an example eye-mountable device 100.

The following detailed description describes various features and functions of the disclosed systems and methods with reference to the accompanying figures. In the figures, similar symbols identify similar components, unless context dictates otherwise. The illustrative system, device and method embodiments described herein are not meant to be limiting. It may be readily understood by those skilled in the art that certain aspects of the disclosed systems, devices and methods can be arranged and combined in a wide variety of different configurations, all of which are contemplated herein.

An electronic device may be utilized to communicate information to a user of the electronic device. Within examples described herein, an ophthalmic device, such as an eye-mountable device or implantable medical device, is provided. The eye-mountable device may include a light source and circuitry to operate the light source. The circuitry and light source may be situated on a substrate embedded in a biocompatible material. The biocompatible material could be a transparent material, such as in a contact lens. For example, the light source may be arranged to emit light through the transparent material so as to be visible to the user. Alternatively, the biocompatible material could be a non-transparent material or could include a transparent portion and a non-transparent portion. For example, the light source may be arranged to emit light through a transparent portion of the biocompatible material so as to visible to the user, while the non-transparent portion blocks ambient light that would otherwise interfere with the visibility of the light from the light source.

In some examples, the biocompatible material is a transparent material in the form of a round lens with a concave surface, which can be removably mounted on a corneal surface overlaying a pupil of an eye, and a convex surface, which faces outward, away from the eye, when the concave surface is mounted on the corneal surface. The substrate may be embedded near the periphery of the transparent material to avoid interference with incident light received closer to the central region of the eye. The light source can be arranged on the substrate to face inward, towards the corneal surface, so as to emit light through the concave surface and into the pupil of the eye. In some examples, the light source is entirely embedded within the transparent material. The circuitry may be configured to cause the light source to emit modulated light that indicates a message to a user of the eye-mountable device. For example, the eye-mountable device may include a sensor that can obtain a reading related to an analyte concentration (e.g., a glucose concentration), temperature, or other parameter, and the modulated light may be indicative of the reading obtained by the sensor.

An optical element can be included in the eye-mountable device to direct and/or focus the modulated light such that the modulated light is viewable through the pupil. For example, where the light source is disposed at the periphery of the transparent material, a lens (e.g., Fresnel lens) can be included to receive the modulated light from an oblique angle and direct the modulated light towards the pupil. In some examples, the optical element can be configured to unfocus (e.g., disperse, etc.) the emitted light to provide a background color viewable through the pupil. For example, the background color can indicate a reading of a sensor (e.g., high glucose level, etc.) or a status of the eye-mountable device.

The eye-mountable device can be powered via radiated energy harvested at the eye-mountable device. Power can be provided by light energizing photovoltaic cells included in the eye-mountable device. Additionally or alternatively, power can be provided by radio frequency energy harvested from an antenna included in the eye-mountable device. A rectifier and/or regulator can be incorporated in the circuitry to generate a stable DC voltage to power the eye-mountable device from the harvested energy. The antenna can be arranged as a loop of conductive material with leads connected to the circuitry. In some embodiments, such a loop antenna can also be used for wireless communication between the eye-mountable device and an external device.

The light emitted by the light source may be modulated by the circuitry by modifying an aspect of the light. For example, color, brightness, intensity or duration of the light emitted by the light source may be modulated such that the modulated light is indicative of a message. For example, the modulated light may include a series of light pulses understandable by the user (e.g., Morse code, etc.) that are indicative of a reading of the sensor. In another example, the color of the modulated light may indicate a status of the eye-mountable device or a status of components included in the eye-mountable device. In another example, the modulated light may be indicative of a message from an external device.

In some examples, the light source can include several light sources (e.g., pixel display, etc.) that form a pattern understandable by the user of the eye-mountable device. For example, the light source can be a display configured to generate an image or shape viewable through the pupil by the user of the eye-mountable device.

Some embodiments of the present disclosure therefore provide systems and methods for intermittently communicating information by modulating the light emitted by the light source. Such an intermittent scheme may reduce total power consumption, because the circuitry and the light source are only powered when the communication is necessary.

In some embodiments, an external device may be configured to provide radio frequency radiation that may be harvested to power the eye-mountable device. In some examples, the external device may be configured to provide light that the photovoltaic cells are configured to harvest power from. Additionally or alternatively, the photovoltaic cells may harvest power from ambient light surrounding the eye-mountable device.

FIG. 1 is a block diagram of an example eye-mountable device 100. The exposed regions of the eye-mountable device 100 are made of a transparent material 110 formed to be contact-mounted to a corneal surface overlaying a pupil of an eye. The eye-mountable device 100 can be configured to provide emitted light 102 that is viewable through the pupil of the eye. In some embodiments, an optical element 112 can be included in the eye-mountable device 100 and configured to direct and/or focus the emitted light 102 such that the emitted light 102 is viewable through the pupil. A substrate 120 is embedded in the transparent material 110 to provide a mounting surface for a power supply 130, circuitry 140, and light source 162. In some embodiments, substrate 120 further comprises an antenna 164 also mounted on the substrate 120. In some embodiments, substrate 120 further comprises a sensor 166 also mounted on the substrate 120. The power supply 130 supplies operating voltages to the circuitry 140. The circuitry 140 provides power and controls the light source 162. The light source 162 is operated by circuitry 140 to provide modulated emitted light 102. In some embodiments, the antenna 164 is operated by circuitry 140 to communicate information to and/or from the eye-mountable device 100. In some embodiments, the sensor 166 receives power and is also operated by circuitry 140 to provide a reading that may be communicated to and/or from the eye-mountable device 100.

To facilitate contact-mounting, the transparent material 110 can have a concave surface configured to adhere ("mount") to a moistened corneal surface overlaying a pupil (e.g., by capillary forces with a tear film coating the corneal surface). Additionally or alternatively, the eye-mountable device 100 can be adhered by a vacuum force between the corneal surface and the transparent material 110 due to the concave curvature. While mounted with the concave surface against the eye, the outward-facing surface of the transparent material 110 can have a convex curvature that is formed to not interfere with eye-lid motion while the eye-mountable device 100 is mounted to the eye. For example, the transparent material 110 can be a curved polymeric disk shaped similarly to a contact lens.

The transparent material 110 can include one or more biocompatible materials, such as those employed for use in contact lenses or other ophthalmic applications involving direct contact with the corneal surface. The transparent material 110 can optionally be formed in part from such biocompatible materials or can include an outer coating with such biocompatible materials. The transparent material 110 can include materials configured to moisturize the corneal surface, such as hydrogels and the like. In some embodiments, the transparent material 110 can be shaped to provide a pre-determined, vision-correcting optical power, such as can be provided by a contact lens.

The optical element 112 can optionally be included in the eye-mountable device 100. The optical element 112 may comprise lens, Fresnel lens, mirrors, prisms, filters or any other component configured to process emitted light 102 propagating towards the optical element 112. The optical element 112 can be configured to direct, reflect and/or focus the emitted light 102 from the light source 162 such that the emitted light 102 is viewable through the pupil of the eye. In some examples, the light source 162 disposed on the substrate 120 and configured to provide the emitted light 102 can be arranged in a periphery of the transparent material 110 to avoid interference with light transmission to the central, light-sensitive region of the eye (e.g., avoid field of view of the eye). In this case, the optical element 112 (e.g., Fresnel lens, mirror, etc.) can be configured to receive the emitted light 102 at an oblique angle and direct the emitted light 102 so that the emitted light 102 is viewable through the pupil. Additionally or alternatively, the optical element 112 can include a plurality of optical elements optically coupled to each other. For example, the optical element 112 may comprise a mirror configured to reflect the emitted light 102 towards a lens configured to focus the emitted light 102 towards the pupil of the eye.

In some embodiments where the optical element 112 is included in the eye-mountable device 100, the optical element 112 can be configured to unfocus (e.g., disperse, etc.) the emitted light 102 such that at least a portion of the emitted light 102 is viewable through the pupil. For example, the optical element 112 can be configured to disperse the emitted light 102 of a given color such that a background color (e.g., the given color) is viewable through the pupil. In some examples, the background color can indicate a message to a user of the eye-mountable device 100, such as a status of the eye-mountable device 100 (e.g., low power, out of range reading from the sensor 166, etc.), the reading of the sensor 166, or information received via the antenna 164. In some examples, the background color may be more viewable when eyelids are in a closed position (e.g., to differentiate background color from ambient light).

Although illustrated in FIG. 1 that the optical element 112 is embedded in the transparent material 110, the optical element 112 can be arranged in other configurations. In some examples, the optical element 112 can be formed into the transparent material 110 such that the transparent material 110 and the optical element 112 are the same physical component. For example, a portion of the transparent material 110 can be formed of a material with a given density and shape to perform the function of directing and/or focusing the emitted light 102. In other examples, the optical element 112 can be incorporated in the light source 162 such that the light source 162 and the optical element 112 are the same physical component. For example, the light source 162 can be manufactured to include the focusing and/or directing function of the optical element 112. In other examples, the optical element 112 can be mounted on the concave surface of the transparent material 110 such that the optical element 112 can be configured to direct and/or focus the emitted light 102 to be viewable through the pupil. For example, the optical element 112 can be mounted on the outside of the transparent material 110 between the concave surface of the transparent material 110 and the corneal surface of the eye. In other examples, the optical element 112 can be an independent device mounted between the eye-mountable device 100 and the corneal surface of the eye and configured to perform the function of directing and/or focusing the emitted light 102 such that the emitted light 102 is viewable through the pupil.

The substrate 120 includes one or more surfaces suitable for mounting the power supply 130, circuitry 140, and light source 162. In some embodiments, the one or more surfaces are also suitable for mounting antenna 164. In some embodiments, the one or more surfaces are also suitable for mounting the sensor 166. The substrate 120 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, through hole pads may be patterned and/or drilled on to the substrate 120 to allow connections between components on more than one side of the substrate 120. For example, some components like circuitry 140 and power supply 130 may be disposed on one side of the substrate 120 and other components like the light source 162 may be disposed on another side of the substrate 120. In some embodiments, the substrate 120 may be a multilayer substrate (e.g., printed circuit board) that allows connections between components included in the eye-mountable device 100 in several layers between multiple sides of the substrate 120. In some embodiments, substantially transparent conductive materials (e.g., indium tin oxide) can be patterned on the substrate 120 to form circuitry 140, electrodes, etc. For example, the antenna 164 can be formed by forming a pattern of gold or another conductive material on the substrate 120 by deposition, photolithography, electroplating, etc. Similarly, interconnects 152 between the circuitry 140 and the light source 162 can be formed by depositing suitable patterns of conductive materials on the substrate 120. In some embodiments, interconnects 154 and 156 may be similarly formed to connect circuitry 140, respectively, with antenna 164 sensor 166. In some embodiments, organic materials (e.g., organometallic chelates, fluorescent dyes, phosphorescent dyes, conjugated dendrimers, other light emitting organic materials, etc.)

can be patterned on the substrate 120 to form, for example, the light source 162. For example, the light source 162 can be an organic light emitting diode (OLED) formed from one or more of the organic materials described above.

A combination of microfabrication techniques including, without limitation, the use of photoresists, masks, deposition techniques, and/or plating techniques can be employed to pattern materials on the substrate 120. In some examples, the substrate 120 can be a rigid material such as polyethylene terephthalate ("PET"), or a flexible material such as polyimide, or other materials configured to structurally support the circuitry 140 and/or chip-based electronics within the transparent material 110. The eye-mountable device 100 can alternatively be arranged with a group of unconnected substrates rather than a single substrate. For example, the circuitry 140 can be mounted to one substrate, while the light source 162 is mounted to another substrate and the two can be electrically connected via interconnects 152.

In some embodiments, the substrate 120 (and other components included in the eye-mountable device 100) can be positioned away from the center of the eye-mountable device 100 and thereby avoid interference with light transmission to the central, light-sensitive region of the eye (e.g., avoid field of view of the eye). For example, where the eye-mountable device 100 is shaped as a concave-curved disk, the substrate 120 can be embedded around the periphery (e.g., near the outer circumference) of the disk. In some embodiments, however, the substrate 120 can be positioned in or near the central region of the eye-mountable device 100. Additionally or alternatively, the substrate 120 (and other components included in the eye-mountable device 100) can be substantially transparent to incoming visible light to mitigate interference with light transmission to the eye.

In some embodiments, the substrate 120 can be shaped as a flattened ring with a radial width dimension sufficient to provide a mounting platform for embedded electronics components. The substrate 120 can have a thickness sufficiently small to allow the substrate 120 to be embedded in the transparent material 110 without influencing a shape of the eye-mountable device 100. The substrate 120 can have a thickness sufficiently large to provide structural stability suitable for supporting electronics mounted thereon. For example, substrate 120 can be shaped as a ring with a diameter of about 10 millimeters, a radial width of about 1 millimeter (e.g., an outer radius 1 millimeter larger than an inner radius), and a thickness of about 50 micrometers. However, the diameter, radial width and thickness values are provided for explanatory purposes only. In some embodiments, the dimensions of the substrate 120 can be selected according to the size and/or shape of the eye-mountable device 100. The substrate 120 can optionally be aligned with the curvature of the convex surface of the eye-mountable device 100.

The power supply 130 is configured to harvest energy to power the circuitry 140 and the light source 162. In some embodiments, the power supply 130 may also be configured to power the antenna 164. In some embodiments, the power supply 130 may also be configured to power the sensor 166. For example, a radio-frequency energy-harvesting antenna 132 can capture energy from incident radio radiation. Additionally or alternatively, photovoltaic cell(s) 134 (e.g., solar cells) can capture energy from incoming ultraviolet, infrared, visible, and/or non-visible radiation. In some embodiments, the incident radio radiation and/or incoming radiation may be ambient radiation in surroundings of the eye-mountable device 100. Additionally or alternatively, the incident radio radiation and/or incoming radiation may be from an external device (not shown in FIG. 1). For example, a head mounted device (e.g., glasses) or other computing device can be configured to provide the incident radio radiation and/or the incoming radiation towards the eye-mountable device 100 for the power supply 130 to harvest energy from. Furthermore, an inertial power scavenging system (not shown in FIG. 1) can be included to capture energy from ambient vibrations. The energy harvesting antenna 132 can optionally be a dual-purpose antenna that is also used to communicate information from/to the eye-mountable device 100. That is, the functions of the antenna 164 and the energy harvesting antenna 132 can be accomplished with a same physical antenna.

In some examples, a rectifier/regulator 136 can be used to condition captured energy to a stable DC supply voltage 138 that is supplied to circuitry 140. For example, the energy harvesting antenna 132 can receive incident radio frequency radiation. Varying electrical signals on the leads of the energy harvesting antenna 132 are output to the rectifier/regulator 136. The rectifier/regulator 136 rectifies the varying electrical signals to a DC voltage and regulates the rectified DC voltage to a level suitable for operating circuitry 140. Additionally or alternatively, output voltage from the photovoltaic cell(s) 134 can be regulated to a level suitable for operating the circuitry 140. The rectifier/regulator 136 can include one or more energy storage devices to mitigate high frequency variations in the energy harvesting antenna 132 and/or photovoltaic cell(s) 134. For example, one or more energy storage devices (e.g., capacitors, inductors, etc.) can be connected with the outputs of the rectifier/regulator 136 to regulate the DC supply voltage 148 and/or configured to function as a low-pass filter.

The circuitry 140 is activated when the DC supply voltage 138 is provided to the circuitry 140, and the logic in the circuitry 140 operates the light source 162 to provide the emitted light 102 that is viewable through the pupil of an eye. In some embodiments, the logic in circuitry 140 also operates antenna 164 to communicate information from/to the eye-mountable device 100. In some embodiments, the logic in circuitry 140 also operates sensor 166 to obtain a reading of the sensor 166. The circuitry 140 can include logic circuitry configured to generate modulation instructions and control the light source 162 to provide modulated emitted light 102 based on the modulation instructions. Additionally or alternatively, in some embodiments, the circuitry 140 may be configured to modulate the emitted light 102 from the light source 162 based on interaction with the antenna 164 and/or sensor 166.

The circuitry 140 can include a modulation interface 142 for modulating light emitted by the light source 162. The circuitry 140 can include logic elements and/or controllers implemented in an integrated circuit to form the modulation interface 142. For example, the modulation interface 142 can modify an aspect of the emitted light 102 by light source 162 like color, brightness, intensity, or duration of the emitted light to provide modulated light. In some examples, the modulation interface 142 can include one or more data lines providing programming information to separately programmed pixels in the light source 162. For example, the light source 162 can be configured, via the programmed pixels, to provide the emitted light 102 comprising a virtual image or pattern viewable through the pupil of the eye.

In some instances, the circuitry 140 may include an antenna interface 144 that is configured to operate antenna 164 to send and/or receive information via antenna 164. The antenna interface 144 can optionally include one or more oscillators, mixers, frequency injectors, etc. to modulate and/or demodulate information on a carrier frequency to be transmitted and/or received by the antenna 164. In some examples, the eye-mountable device 100 is configured to indicate an output from sensor 166 by modulating an impedance of the antenna 164 in a manner that is perceivable by an external device (not shown in FIG. 1). For example, the antenna interface 144 can cause variations in the amplitude, phase, and/or frequency of radio frequency radiation (RF radiation) from the antenna 164, and such variations can be detected by the external device. In some examples, the RF radiation may be indicative of the reading of the sensor 166 or of a status of the eye-mountable device 100 (e.g., malfunctioning power supply, reading of sensor out of range, etc.). The RF radiation may also include radiation from the external device to the antenna 164. In some examples, the eye-mountable device 100 is configured to receive the RF radiation from the external device that is indicative of a message or of modulation instructions for the light source 162. For example, circuitry 140 may modulate light emitted by the light source 162 based on the message (e.g., define meaning of color modulated by circuitry 140, communicate information to a user of the eye-mountable device, indicate a status of the external device, etc.). In other examples, the circuitry 140 may control components included in the substrate 120 based on the message. The antenna interface 144 can be connected to antenna 164 via interconnects 154. In some examples, the antenna 164 can be formed by patterning conductive materials (e.g., gold, etc.) onto the substrate 120.

Although not illustrated in FIG. 1, additionally or alternatively to the antenna 164, the circuitry 140 can include a photodetector configured to receive information and/or instructions from an external device via incident light on the photodetector. In this case, the photodetector can be, for example, an active pixel sensor (APS), charge-coupled device (CCD), cryogenic detector, photodiode, photoresistor, phototransistor, camera, or any other sensor of light configured to receive incident light indicative of the information and/or instructions. For example, the external device can be a computing device (e.g., head mounted device, mobile phone, portable computer, etc.) and the incident light can be non-visible light (ultraviolet, infrared, etc.) indicative of the information and/or instructions. The incident light can be used to operate the eye-mountable device 100 through the circuitry 140 similarly to the RF radiation received by the antenna 164 as described above. For example, the circuitry 140 may modulate light emitted by light source 162 based on the incident light on the photodetector. In other examples, the circuitry 140 may control components included in the eye-mountable device 100 based on the incident light.

In some examples, the photodetector (not shown in FIG. 1) can be configured to receive reflected light from the eye. For example, the light source 162 can be configured to generate emitted light 102 that is non-visible (e.g., infrared, ultraviolet, etc.). In this example, the photodetector can receive reflected light from the eye due to the non-visible emitted light 102 and communicate data indicative of the reflected light to circuitry 140. Thus, in this example, the circuitry 140 can determine a structure included in the eye (e.g., retina structure) and modulate the emitted light 102 according to the determination or communicate information via antenna 164 based on the determination. For example, the emitted light 102 can be modulated to a visible color or intensity based on the determination from the reflected light. In another example, the information communicated via antenna 164 can indicate the determined structure.

The circuitry 140 can optionally include a sensor interface 146 for operating sensor 166. The sensor 166 can be, for example, a bio-sensor configured to measure an analyte in the tear film on the corneal surface or on the convex surface of the transparent material 110 when the concave surface is mounted on the corneal surface. For example, the sensor 166 can be a glucose sensor configured to provide a reading relating to glucose level in the tear film. In some examples, the sensor 166 may measure other biological information like blood pressure, temperature, heart rate or psychological state of the user of the eye-mountable device 110. For example, the sensor 166 can be configured to measure a frequency of eye-blinks to determine the psychological state of the user. In some examples, the sensor 166 may measure aspects of a surrounding environment of the user. For example, the sensor 166 may measure the ambient light intensity or humidity of the surrounding environment. For example, the circuitry 140 may be configured to modulate the intensity of the emitted light 102 by the light source 102 according to the intensity of ambient light indicated by the reading of the sensor 166. In this example, the emitted light 102 can be modulated to be viewable through the pupil against bright ambient light conditions and/or emitted light 102 can be modulated not to be too bright in dark ambient light conditions. In other examples, the modulated emitted light 102 may be indicative of the reading of the sensor (e.g., red color may indicate high glucose level, etc.).

The circuitry 140 is connected to the light source 162 via interconnects 152. For example, where the circuitry 140 includes logic elements implemented in an integrated circuit to control the light source 162, a patterned conductive material (e.g., gold, platinum, palladium, titanium, copper, aluminum, silver, metals, combinations of these, etc.) can connect a terminal on the chip to the light source 162. In some embodiments, the circuitry 140 can be similarly connected to the antenna 164 via interconnects 154. In some embodiments, the circuitry 140 can be similarly connected to the sensor 166 via interconnects 156.

The light source 162 can include one or more light emitting diodes (LED), vertical cavity surface emitting lasers (VCSEL), organic light emitting diodes (OLED), polymer light-emitting diodes (PLED), light emitting polymers (LEP), liquid crystal displays (LCD), microelectromechanical systems (MEMS), or any other device configured to selectively transmit, reflect, and/or emit light according to information from the modulation interface 142 via the interconnects 152 to provide the modulated emitted light 102. In some examples, the emitted light 102 can include visible light. In other examples, the emitted light 102 can include non-visible light (e.g., infrared, ultraviolet, etc.).

In some examples, the light source 162 can be configured as an independent physical component (e.g., a gallium nitride LED) and arranged to provide the emitted light 102 viewable through the pupil. In other examples, the light source 162 and the substrate 120 can be the same physical component. For example, organic materials (e.g., organometallic chelates, fluorescent dyes, phosphorescent dyes, conjugated dendrimers, other light emitting organic materials, etc.) can be patterned on the substrate 120 to form the light source 162 (e.g., OLED, PLED, LEP, etc.). In other examples, the light source 162 can be configured to process ambient light to provide the emitted light 102. For example, the light source 162 can include a substantially transparent liquid crystal material arranged along a path of ambient light towards the pupil of the eye and configured to provide the emitted light 102 based on modulation instructions from the modulation interface 142 via the interconnects 152. Thus, in this case, the modulated emitted light 102 is provided due to chemical properties of the liquid crystal material and the modulation instructions from the modulation interface 142 included in circuitry 140.

In some examples, the light source 162 may include an array of LEDs configured, via the modulation interface 142, to provide the emitted light 102 including multiple colors, intensities, and shapes. For example, the emitted light 102 can be a virtual image viewable through the pupil and formed by the light source 162 based on modulation instructions from the modulation interface 142 included in the circuitry 140.

In some examples, the light source 162 may also include the optical element 112 to direct and/or focus the emitted light 102 through the concave surface of the transparent material 110 and towards the corneal surface such that the emitted light 102 is viewable through the pupil of the eye when the concave surface of the transparent material 110 is mounted on the corneal surface. For example, the light source 162 and the optical element 112 can be the same physical component.

It is noted that the block diagram shown in FIG. 1 is described in connection with functional modules for convenience in description. For example, while the functional blocks in FIG. 1 shown as the power supply block 130 and circuitry block 140 can be implemented by separately packaged chips electrically connected to one another, they do not necessarily need to be implemented as physically separated modules. The embodiments of the eye-mountable device 100 can be arranged with one or more of the functional modules ("subsystems") implemented in a single chip, integrated circuit, and/or physical component. For example, while the rectifier/regulator 136 is illustrated in the power supply block 130, the rectifier/regulator 136 can be implemented in a chip that also includes the logic elements of circuitry 140 and/or other features of the embedded electronics in the eye-mountable device 100. Thus, the DC supply voltage 138 that is provided to the circuitry 140 from the power supply 130 can be a supply voltage that is provided to components on a chip by rectifier and/or regulator 136 components located on a same chip.

Additionally or alternatively, the energy harvesting antenna 132 and the antenna 164 can be implemented with the same physical antenna. For example, a loop antenna can both harvest incident radiation for power generation and communicate information via radio frequency radiation.

In some embodiments, the eye-mountable device 100 can operate to non-continuously ("intermittently") supply energy by the power supply 140. For example, incident RF radiation can be supplied to the energy harvesting antenna 132 to power the eye-mountable device 100 long enough to obtain a reading by the sensor 166 and wirelessly communicate the reading via antenna 164. In such an example, the RF radiation can be considered an interrogation signal from an external device to the eye-mountable device 100 to request a reading. By periodically interrogating the eye-mountable device 100 (e.g., by supplying RF radiation to temporarily turn the device on), the external device can accumulate a series of readings without continuously powering the eye-mountable device 100.

Figure 2A:
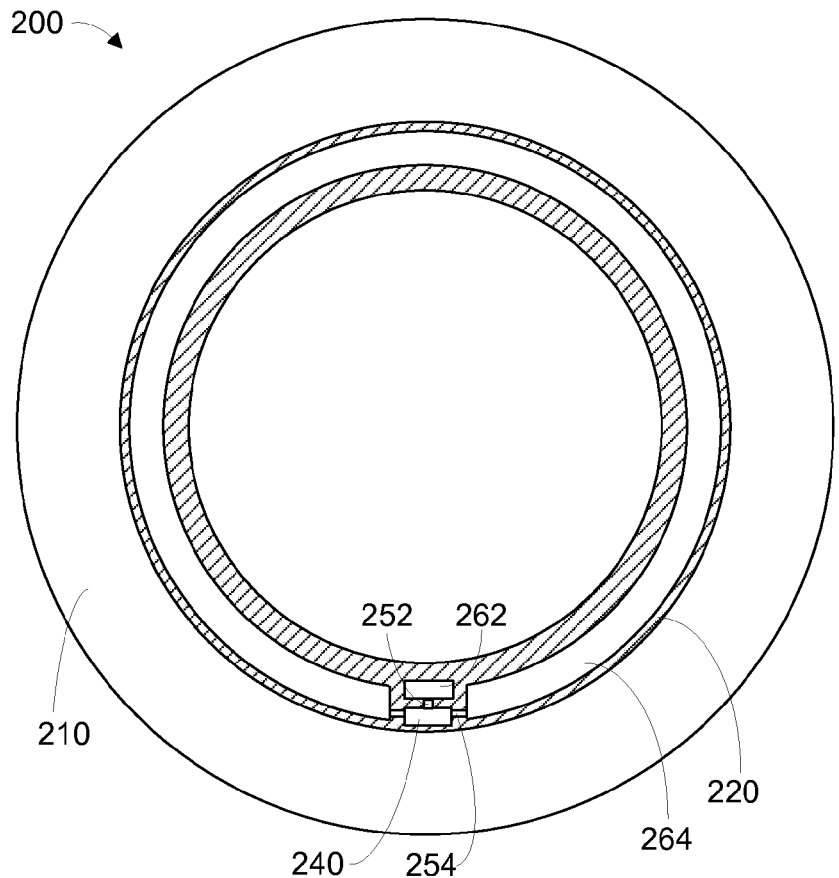
FIG. 2A is a bottom view of an example eye-mountable device 200.
Figure 2B:
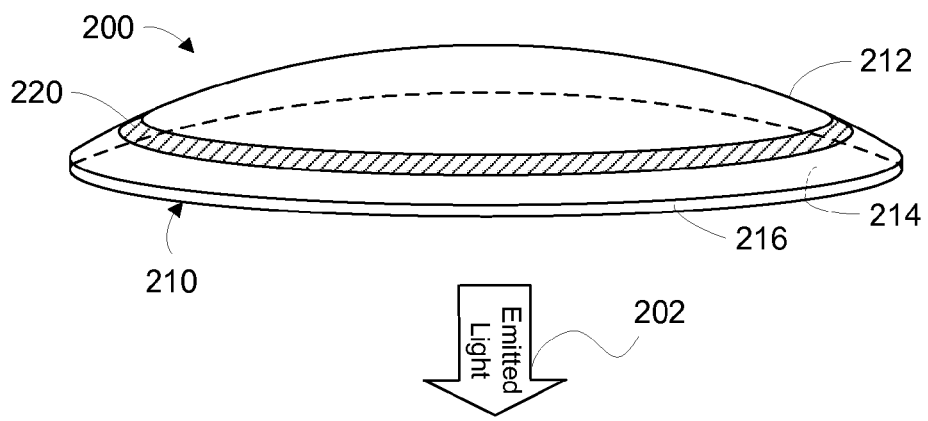
FIG. 2B is a side view of the example eye-mountable device shown in FIG. 2A.

FIG. 2A is a bottom view of an example eye-mountable device 200 (or ophthalmic device). FIG. 2B is a side view of the example eye-mountable device 200 shown in FIG. 2A. It is noted that the relative dimensions in FIGS. 2A and 2B are not necessarily to scale, but have been rendered for purposes of explanation only in describing the arrangement of the example eye-mountable device 200. The eye-mountable device 200 can be formed of a transparent material 210 shaped as a curved disk. The transparent material 210 can allow incident light (e.g., field of view of the eye) to be transmitted to the eye while the eye-mountable device 200 is mounted to the eye. In some examples, the transparent material 210 can be a biocompatible polymeric material similar to those employed to form vision correction and/or cosmetic contact lenses in optometry, such as polyethylene terephthalate (PET), polymethyl methacrylate (PMMA), polyhydroxyethylmethacrylate (polyHEMA), silicone hydrogels, combinations of these, etc. The transparent material 210 can be formed with one side having a concave surface 214 (bottom-view surface shown in FIG. 2A) suitable to fit over a corneal surface of the eye. The opposite side of the disk can have a convex surface 212 that does not interfere with eyelid motion while the eye-mountable device 200 is mounted to the eye. A circular outer side edge 216 can connect the concave surface 214 and the convex surface 212.

The eye-mountable device 200 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 200 can be selected according to the size and/or shape of the corneal surface of the wearer's eye.

The transparent material 210 can be formed with a curved shape in a variety of ways. For example, techniques similar to those employed to form vision-correction contact lenses, such as heat molding, injection molding, spin casting, etc. can be employed to form the transparent material 210. When the eye-mountable device 200 is mounted to an eye, the convex surface 212 faces outward to an ambient environment while the concave surface 214 faces inward, toward the corneal surface. The convex surface 212 can therefore be considered an outer, top surface of the eye-mountable device 200 whereas the concave surface 214 can be considered an inner, bottom surface. The "bottom" view shown in FIG. 2A is facing the concave surface 214.

A substrate 220 is embedded in the transparent material 210. In some examples, the substrate 220 can be embedded to be along an outer periphery of the transparent material 210, away from a central region of the eye-mountable device 200. Thus, in this example, the substrate 220 does not interfere with vision because it is too close to the eye to be in focus and is positioned away from the central region where ambient light is transmitted to eye-sensing portions of the eye. In some examples, the substrate 220 can be formed of a second transparent material to further mitigate effects on visual perception.

The substrate 220 can be shaped as a flat, circular ring (e.g., a disk with a centered hole). The flat surface of the substrate 220 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. In some examples, the flat surface of the substrate 220 is also a platform for patterning organic materials (e.g., via microfabrication techniques discussed above) to form light sources. In some examples, the substrate 220 and the transparent material 210 can be substantially cylindrically symmetric about a common central axis. The substrate 220 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 220 can be implemented in a variety of different form factors, similar to the discussion of the substrate 120 in connection with FIG. 1 above.

Circuitry 240, a light source 262, and a loop antenna 264 are disposed on a side of the substrate 230 that is facing the concave surface 214 ("bottom side") of the transparent material 210 as shown in FIG. 2A. However, in some embodiments, the circuitry 240, the light source 262, and the loop antenna 264 may be disposed on any side of the substrate 220. For example, in some embodiments, the circuitry 240 may be disposed in the opposite side ("top side") of the substrate 220 that is facing the convex surface 212 of the transparent material 210. In one example, the light source 262 may be disposed in the side of the substrate 220 that is facing the convex surface 212 ("top side"). In that case, the substrate 220 may include a hole through which emitted light 202 by the light source 262 can reach the concave surface 214 and propagate towards the corneal surface such that the emitted light 202 is viewable through a pupil of the eye. In some examples, one or more components disposed on the substrate 220 may be disposed on a side of the substrate 220 that is facing the circular outer side edge 216 of the transparent material 210.

In some embodiments not illustrated in FIGS. 2A-2B, the substrate 220 may include multiple layers for interconnects and other conductive material connected to components disposed on the substrate 220. Other configurations of the substrate 220 are contemplated herein and may be obvious to those of ordinary skill in the art. For example, one of the multiple layers may be utilized as "a ground plane" for the components to connect to a ground voltage. In an example where the antenna 264 is disposed on the "top side" of the substrate 220 (e.g., the side facing the convex surface 212), interconnects 254 may be arranged in a through hole connecting the side of the substrate 220 that is facing the concave surface 214 ("bottom side") of the transparent material 210 to the opposite side of the substrate 220 that is facing the convex surface 212 ("top side") of the transparent material 210 to connect the circuitry 240 to the loop antenna 264.

The circuitry 240 may comprise a chip including logic elements configured to operate the loop antenna 264 and the light source 262. The circuitry 240 is electrically coupled to the light source 262 and the loop antenna 264, respectively, by interconnects 252 and 254. The interconnects 252, 254, and the loop antenna 264 can be formed from conductive materials patterned on the substrate 220 by a process for patterning such materials, such as deposition, photolithography, etc. The conductive materials patterned on the substrate 220 can be, for example, gold, platinum, palladium, titanium, carbon, aluminum, copper, silver, silver-chloride, conductors formed from noble materials, metals, combinations of these, etc. In some examples, the light source 262 (e.g., OLED) can be formed from organic materials patterned on the substrate 220 by a process for patterning such materials, such as deposition. The organic materials patterned on the substrate 220 can be, for example, organometallic chelates, fluorescent dyes, phosphorescent dyes, etc. The circuitry 240 can be configured to modulate emitted light 202 from the light source 262 to provide modulated light that is viewable through the pupil of the eye when the eye-mountable device 200 is mounted on the corneal surface.

The loop antenna 264 can be a layer of conductive material patterned along a flat surface of the substrate to form a flat conductive ring. In some instances, the loop antenna 264 can be formed without making a complete loop. For instance, the loop antenna 264 can have a cutout to allow room for the circuitry 240 and the light source 262, as illustrated in FIG. 2A. However, the loop antenna 264 can also be arranged as a continuous strip of conductive material that wraps entirely around the flat surface of the substrate 220 one or more times. For example, a strip of conductive material with multiple windings can be patterned on a side of the substrate 220 opposite the circuitry 240 and the light source 262. Thus, in this example, interconnects 254 between the ends of such a wound antenna (e.g., antenna leads) can then be passed through the substrate 220 to the circuitry 240. In some examples, the loop antenna 264 can be configured to harvest energy from incident radio frequency radiation on the eye-mountable device 200. In some instances, the loop antenna 264 can be replaced by, or supplemented with a photovoltaic cell (e.g., solar cells) configured to harvest the energy from ambient light surrounding the eye-mountable device 200.

The light source 262 may include one or more light emitting diodes (LED), vertical cavity surface emitting lasers (VCSEL), organic light emitting diodes (OLED), liquid crystal display (LCD), microelectromechanical system (MEMS), or any other device configured to selectively transmit, reflect, and/or emit light according to received modulation instructions from the circuitry 240 via the interconnects 252 to provide the modulated emitted light 202. Operation of the light source 262 is similar to light source 162 discussed in FIG. 1. The light source 262 is configured to provide the emitted light 202 through the concave surface 214 and towards the corneal surface such that the emitted light 202 is viewable through the pupil of the eye. In some examples where a plurality of light sources are included in the light source 262, the plurality of light sources can be arranged in any arrangement compatible with the substrate 220. In some examples, four light sources (e.g., LEDs) can be arranged at different locations along a circumference of the substrate 220 and connected to circuitry 240 via the interconnects 252. For example, the four light sources can be placed at 12, 3, 6, and 9 o'clock positions along the circumference of substrate 220. In some examples, the emitted light 202 can include visible light. In other examples, the emitted light 202 can include non-visible light (e.g., infrared, ultraviolet, etc.).

The light source 262 may be configured in a rectangular, triangular, circular and/or any shape that is compatible with the flat surface of the substrate 220. For example, the light source 262 may have a loop shape similar to the loop antenna 264. The light source 262 may be configured to provide the emitted light 202 based on modulation instructions from the circuitry 240. For example, the emitted light 202 may be indicative of a status of the eye-mountable device 200 or a status of components included in the eye-mountable device 200. For example, the emitted light 202 may be a blinking light that indicates insufficient power being provided to the eye-mountable device 200.

FIG. 2C is a side cross-section view of the example eye-mountable device 200 shown in FIGS. 2A and 2B while mounted to a corneal surface 20 of an eye 10. FIG. 2D is a close-in side cross-section view enhanced to show the substrate 220 embedded in the transparent material 210, the light source 262, and the emitted light 202 in the example eye-mountable device 200 when mounted as shown in FIG. 2C. It is noted that relative dimensions in FIGS. 2C and 2D are not necessarily to scale, but have been rendered for purposes of explanation only in describing the arrangement of the example eye-mountable device 200. Some aspects are exaggerated to allow for illustration and facilitate explanation. It is further noted that the orientation of the substrate 220 embedded in the transparent material 210 is not necessarily as shown in FIG. 2D. In some embodiments, the substrate 220 may be oriented at any angle such that an outward-facing flat mounting surface 222 of the substrate 220 is facing the convex surface 212 of the transparent material 210 and an inward-facing flat mounting surface 224 of the substrate 220 is facing the concave surface 214 of the transparent material 210.

The eye 10 includes a corneal surface 20 that is covered by bringing an upper eyelid 30 and a lower eyelid 32 together over eye 10. Ambient light is received by the eye 10 through the corneal surface 20 and through a pupil 40, where the ambient light is optically directed to light sensing elements of the eye 10 (e.g., rods and cones, etc.) to stimulate visual perception. As illustrated in FIG. 2C, the concave surface 214 is configured to be removably mounted to the corneal surface 20. Additionally, the convex surface 212 is compatible with motion of the eyelids 30 and 32.

As illustrated in FIG. 2D, the emitted light 202 from the light source 262 is directed towards the corneal surface 20, through the concave surface 214, and through the pupil 40 when the concave surface 214 is mounted on the corneal surface 20. For example, the light source 262 can be disposed on the inward-facing flat mounting surface 224 of the substrate 220 to allow the emitted light 202 to travel through the concave surface 214. In the example, interconnects 252 connect the circuitry 240 to the light source 262.

As shown in the cross-sectional views in FIGS. 2C and 2D, the substrate 220 can be inclined such that the flat mounting surfaces 222 and 224 are approximately parallel to an adjacent portion of the concave surface 214. However, in some embodiments, the substrate 220 can be oriented at any angle such that the inward-facing mounting surface 224 is facing the concave surface 214. As described above, the substrate 220 can be a flattened ring with the inward-facing surface 224 (closer to the concave surface 214 of the transparent material 210) and the outward-facing surface 222 (closer to the convex surface 212). The substrate 220 can have electronic components, patterned organic materials and/or patterned conductive materials mounted to either or both mounting surfaces 222, 224 or through the substrate 220 to connect components from one surface to another.

Although not illustrated in FIGS. 2A-2D, the eye-mountable device 200 can further include an optical element similarly to the optical element 112 in the discussion of FIG. 1 (e.g., lens, Fresnel lens, mirror, prism, filter, etc.) along the path of the emitted light 202. For example, the optical element can be configured to focus the emitted light 202 such that the emitted light 202 is viewable through the pupil 40.

Although not illustrated in FIGS. 2A-2D, the eye-mountable device 200 can further include a sensor (similarly to sensor 166 in FIG. 1) electrically coupled to the circuitry 240 and configured to provide a reading. For example, a glucose sensor can be included to provide a reading related to a level of glucose in a tear film of the eye 10. Thus, in this example, the circuitry 240 can be configured to modulate the emitted light 202 from the light source 262 to indicate the reading of the glucose sensor (e.g., red for high level, green for normal level, etc.).

Figure 3:
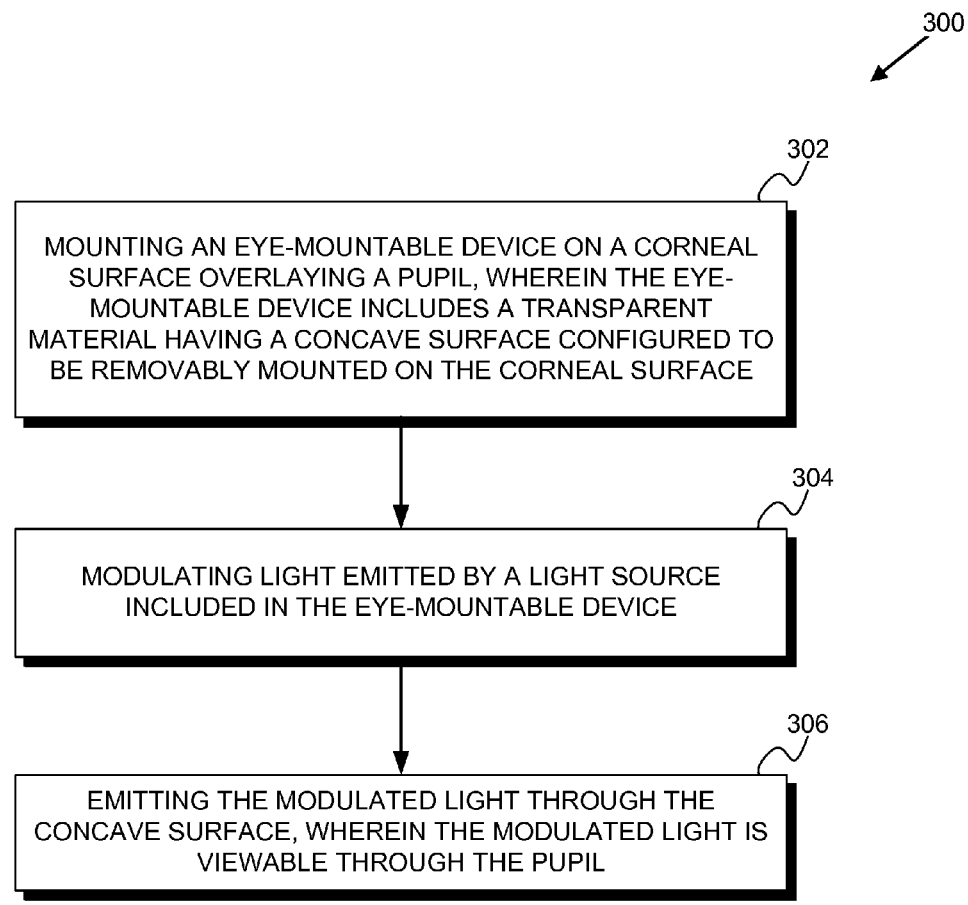
FIG. 3 is a block diagram of an example method 300 for operating an eye-mountable device, in accordance with at least some embodiments described herein.

FIG. 3 is a block diagram of an example method for operating an eye-mountable device, in accordance with at least some embodiments described herein. Method 300 shown in FIG. 3 presents an embodiment of a method that could be used with the devices 100 and 200, for example. Method 300 may include one or more operations, functions, or actions as illustrated by one or more of blocks 302-306. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 300 and other processes and methods disclosed herein, the flowchart shows functionality and operation of one possible implementation of present embodiments. In this regard, each block may represent a module, a segment, or a portion of a manufacturing or operation process.

At block 302, the method 300 includes mounting an eye-mountable device on a corneal surface overlaying a pupil, wherein the eye-mountable device includes a transparent material having a concave surface configured to be removably mounted on the corneal surface.

At block 304, the method 300 includes modulating light emitted by a light source included in the eye-mountable device.

In some examples, modulation instructions can be generated by circuitry included in the eye-mountable device. In one example, the circuitry can generate the modulation instructions based on a status of the eye-mountable device (e.g., low power available, malfunctioning component, etc.). In another example, the circuitry can generate the modulation instructions based on a reading of a sensor included in the eye-mountable device (e.g., a high glucose reading of a glucose sensor). In another example, the circuitry can generate the modulation instructions based on data and/or instructions received from an external device (e.g., a computing device). For example, the data can indicate a time of day, and the circuitry can generate the modulation instructions to modulate the light to a color suitable for the time of day (e.g., green at morning, blue at midday, red at night, etc.).

Additionally or alternatively, in some examples, the eye-mountable device can receive the modulation instructions from an external device (e.g., head-mounted device, mobile phone, computing device, etc.). In one example, the external device can send the modulation instructions indicative of modulating the light to a certain color or brightness (e.g., a user selected setting, etc.). In another example, the modulation instructions can relate to a message from the external device (e.g., alert a wearer of the eye-mountable device that they received an email, communicate content of the email, etc.). In this example, the messaged can be relayed via the modulated light corresponding to a communication code (e.g., Morse code) or by displaying the message (e.g., via a virtual image). In some examples, the external device can send the modulation instructions via radio frequency radiation (RF radiation), and the eye-mountable device can include an antenna configured to receive the RF radiation.

At block 306, the method 300 includes emitting the modulated light through the concave surface, wherein the modulated light is viewable through the pupil.

Although not illustrated in block 306, the eye-mountable device can include an optical element along the path of the modulated light configured to focus and/or unfocus the modulated light such that the modulated light is viewable through the pupil. For example the optical element can be similar to optical element 112 included in the discussion for FIG. 1.

In some examples for method 300, the eye-mountable device may be mounted on a corneal surface of a user's eye (step 302). In one example, the eye-mountable device may detect that low power is being supplied to the eye-mountable device. Thus, the method 300 can include modulating light emitted by a light source included in in the eye-mountable device to indicate the low power (e.g., flashing red light) (step 302), and emitting the modulated light (step 306) through the concave surface and towards the corneal surface (similarly to the emitted light 202 in the embodiment illustrated in FIG. 2D) such that the modulated light is viewable through a pupil of the eye.

Figure 4:
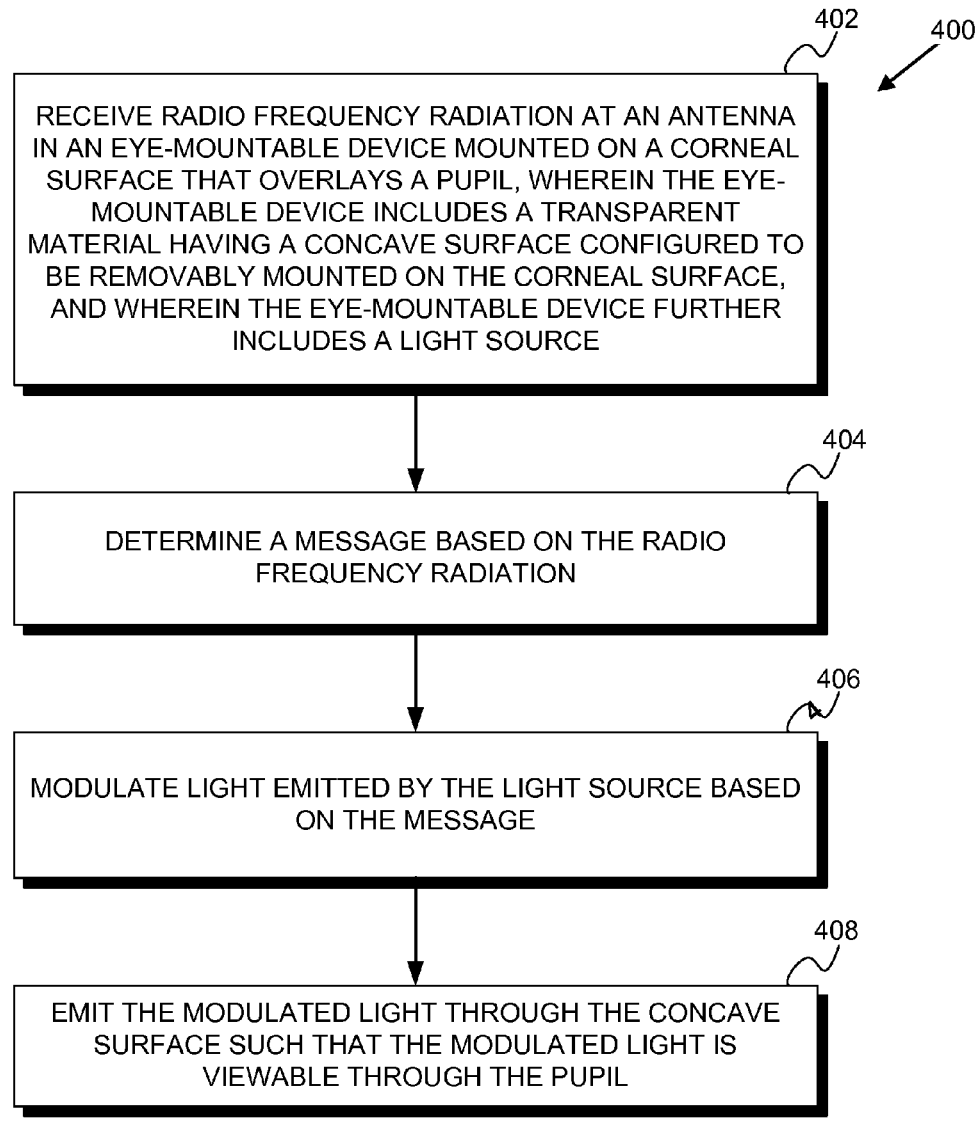
FIG. 4 is a block diagram of an example method 400 for operating an eye-mountable device via an antenna, in accordance with at least some embodiments described herein.

FIG. 4 is a block diagram of an example method 400 for operating an eye-mountable device via an antenna, in accordance with at least some embodiments described herein. Method 400 shown in FIG. 4 presents an embodiment of a method that could be used with the devices 100 and 200, for example. Method 400 may include one or more operations, functions, or actions as illustrated by one or more of blocks 402-408. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 400 and other processes and methods disclosed herein, the flowchart shows functionality and operation of one possible implementation of present embodiments. In this regard, each block may represent a module, a segment, or a portion of a manufacturing or operation process.

At block 402, radio frequency radiation is received at an antenna in an eye-mountable-device mounted on a corneal surface that overlays a pupil. The eye-mountable device includes a transparent material having a concave surface configured to be removably mounted on the corneal surface. The eye-mountable device further includes a light source.

At block 404, the eye-mountable device determines a message based on the radio frequency radiation (e.g., the message can relate to modulating light emitted by the light source).

At block 406, the eye-mountable device modulates light emitted by the light source based on the message (e.g., emit light pulses indicative of the message).

At block 408, the eye-mountable device emits the modulated light through the concave surface such that the modulated light is viewable through the pupil.

In one example, the radio frequency radiation may pertain to modulation instructions ("message") for the eye-mountable device (step 402). For example, the radio frequency radiation may indicate a message (step 404) that defines the modulation of light according to each alert type for a user of the eye-mountable device (e.g., define color for low power, define color for time of day alert, etc.). Thus, in this example, the eye-mountable device may then modulate the light emitted by the light source based on the alert type ("message") and according to the modulation instructions (step 406). The light source may then emit the modulated light through the concave surface and towards the corneal surface such that the modulated light is viewable through the pupil to alert the user of the alert according to the defined color for the alert (step 408).

Figure 5:
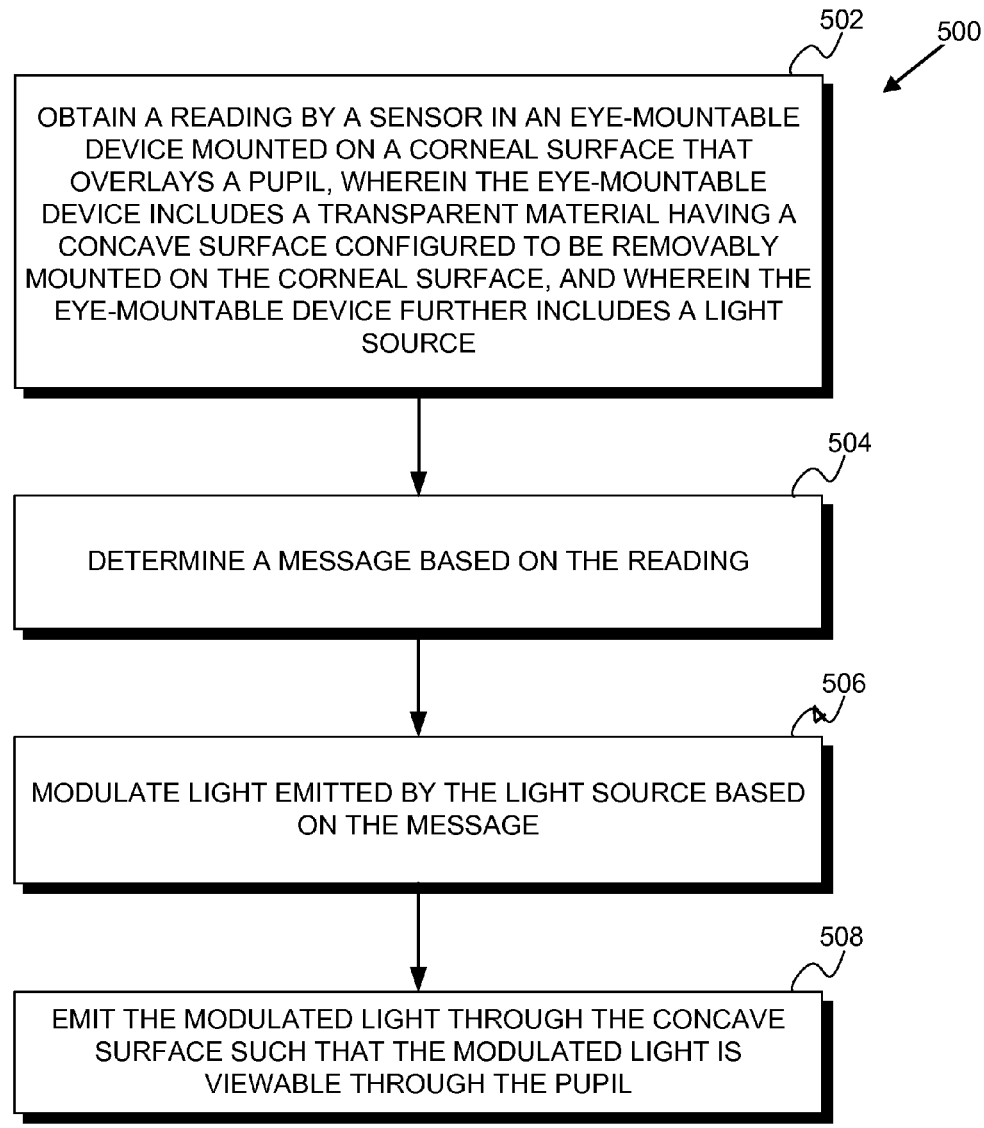
FIG. 5 is a block diagram of an example method 500 for operating an eye-mountable device to communicate a sensor reading.

FIG. 5 is a block diagram of an example method 500 for operating an eye-mountable device to communicate a sensor reading, in accordance with at least some embodiments described herein. Method 500 shown in FIG. 5 presents an embodiment of a method that could be used with the devices 100 and 200, for example. Method 500 may include one or more operations, functions, or actions as illustrated by one or more of blocks 502-508. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 500 and other processes and methods disclosed herein, the flowchart shows functionality and operation of one possible implementation of present embodiments. In this regard, each block may represent a module, a segment, or a portion of a manufacturing or operation process.

At block 502, a reading by a sensor in an eye-mountable device is obtained. The eye-mountable device is mounted on a corneal surface that overlays a pupil. The eye-mountable device includes a transparent material having a concave surface configured to be removably mounted on the corneal surface. The eye-mountable device further includes a light source.

At block 504, the eye-mountable device determines a message based on the reading (e.g., the message can relate to a glucose reading obtained by a sensor).

At block 506, the eye-mountable device modulates light emitted by the light source based on the message (e.g., emit blinking red light to alert a user of an abnormally high or abnormally low glucose reading).

At block 508, the eye-mountable device emits the modulated light through the concave surface such that the modulated light is viewable through the pupil.

For example, the eye-mountable device may include a sensor configured to provide a measurement of an analyte in a tear film (e.g., glucose) when the concave surface is mounted on the corneal surface. Thus, the method 500 could include obtaining a reading of the sensor (step 502), determining a message (step 504) based on the reading (e.g., level of glucose, etc.), modulating the light emitted (step 506) by the light source (e.g., red color for high reading, green color for normal reading, blue color for low reading), and emitting the modulated light (step 508) through the concave surface and towards from the corneal surface (similarly to the emitted light 202 in the embodiment illustrated in FIG. 2D) such that the modulated light is viewable through the pupil. In some examples, the modulated light can be indicative of a message from the eye-mountable device. In some examples, the message may relate to a status of the eye-mountable device (e.g., low power remaining).

Figure 6A:
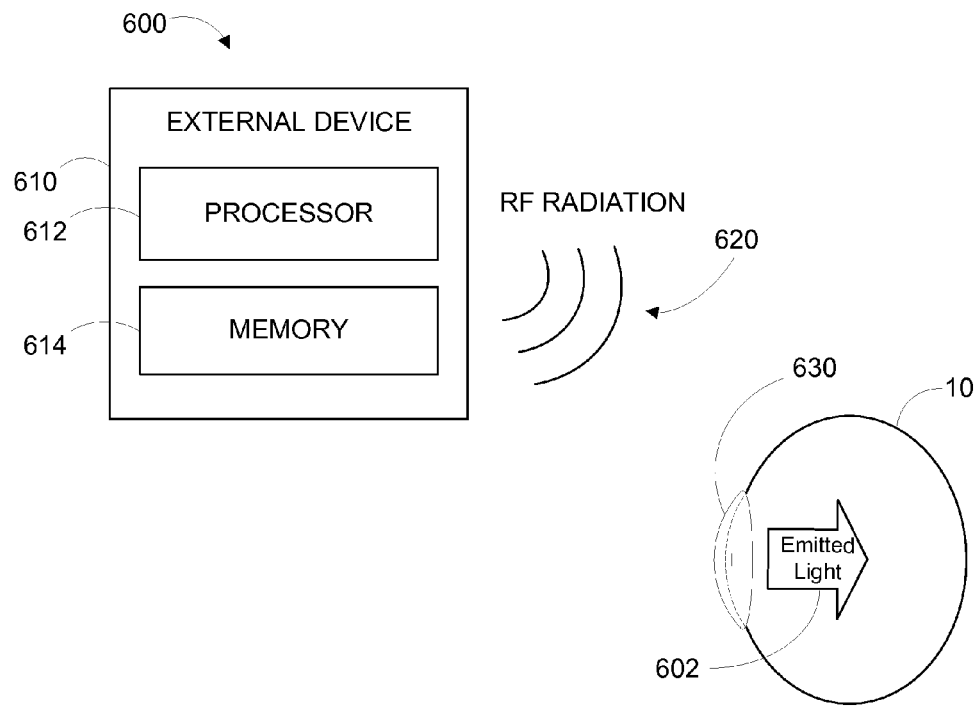
FIG. 6A is a block diagram of an example system 600 with an eye-mountable device that includes an inward facing light source and is operated by an external device.

FIG. 6A is a block diagram of an example system 600 with an eye-mountable device 630 that includes an inward facing light source and is operated by an external device 610. The eye-mountable device 630 can be configured to be contact-mounted over a corneal surface overlaying a pupil of an eye 10. The eye-mountable device 630 can be configured to receive radio frequency radiation (RF radiation) 620 from the external device 610, and modulate emitted light 602 such that the emitted light 602 is viewable through the pupil.

The external device 610 can be a smart phone, digital assistant, head-mounted computing device (e.g., eye glasses with computing capability), or other computing device with wireless connectivity sufficient to provide the RF radiation 620. The external device 610 can also be implemented as an antenna module that can be plugged in to a computing device, such as in an example where the RF radiation 602 operates at carrier frequencies not commonly employed in computing devices. The external device 610 can also be implemented as a broadcasting antenna such as a cell phone tower or a satellite. In some instances, the external device 610 is a special-purpose device configured to be worn relatively near to a wearer's eye, allowing communication via the RF radiation 620 with a low power budget. For example, the external device 610 can be integrated in a piece of jewelry such as a necklace, earring, etc. or integrated in an article of clothing worn near the head, such as a hat, headband, eyeglasses, etc.

In some examples, the external device 610 can be configured to send and/or receive information to/from the eye-mountable device 630 via the RF radiation 620. In some examples, the external reader 610 may provide the RF radiation 620 to an energy harvesting antenna included in the eye-mountable device 630 that is configured to harvest the RF radiation 620 to provide power to the eye-mountable device 630.

The external device 610 includes a processor 612 and a memory 614. The processor 612 can be a computing system that executes software stored in the memory 614 to cause system 600 to operate, as described herein, the eye-mountable device 630. The external device 610 can also include an antenna (not shown) for transmitting radio frequency radiation 620 (RF radiation) that is received by the eye-mountable device 630. For example, the RF radiation 620 may correspond to modulation instructions for the light source included in the eye-mountable device 630. The external device 610 can be configured to provide the modulation instructions to modify an aspect of the emitted light 602 (e.g., color, brightness, intensity, duration, etc.) viewable through the pupil of the eye 10.

For instance, the external device 610 may be a hand-held computing device (e.g. mobile phone, personal digital assistant, etc.). In such an example, a user of system 600 may select the appearance (color, intensity, frequency, etc.) of the emitted light 602 as the user wishes. Thus, the user can configure modulation of the emitted light 602 using the external device 610. For example, the user may want to change the brightness of the emitted light 602. Thus, the external reader 610 can send modulation instructions to the eye-mountable device 630 pertaining to the selected modulation by the user. As a result, the eye-mountable device 630 can modulate the emitted light 602 to reflect the user's selections. In other examples, the modulation instructions may be determined based on instructions in the memory 614. For example, the modulation instructions may be indicative of an appointment in a calendar of the user determined by the external reader 610. For example, the eye-mountable device 630 may modulate the emitted light 602 (e.g. flashing red light) to indicate to the user an upcoming appointment.

In some examples, the RF radiation 620 can indicate a message from the external device 610 to the user. For example, the external device 610 (e.g., smartphone, etc.) can receive a text message for the user ("a message"). The RF radiation can indicate modulation instructions to communicate contents of the text message to the user via the emitted light 602. For example, the eye-mountable device 630 can be configured to provide modulated emitted light 602 indicative of the text message in a code understandable to the user (e.g., Morse code).

In some examples, the RF radiation 620 can indicate a status of the external device 610. For example, the RF radiation 620 can indicate that the external device 610 is low on power. The eye-mountable device 630 may then modulate the emitted light 602 to indicate to the user that the external device 610 is low on power. For example, the emitted light 602 can be a blinking yellow light that indicates to the user that the external device 610 is low on power.

In some examples, the RF radiation 620 can include information transmitted from the eye-mountable device 630 to the external device 610. For example, the eye-mountable device 630 can include a sensor configured to measure an analyte (e.g., glucose) in a tear film of the eye 10. The eye-mountable device 630 can transmit the reading to the external device 610 via the RF radiation 620 using an antenna included in the eye-mountable device 630.

Figure 6B:
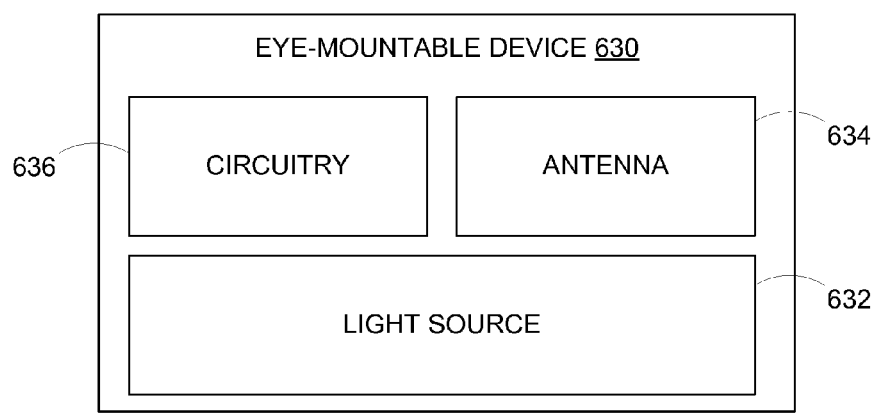
FIG. 6B is a block diagram of the eye-mountable device 630 described in connection with FIG. 6A.

FIG. 6B is a block diagram of the eye-mountable device 630 described in connection with FIG. 6A. The eye-mountable device 630 includes an inward facing light source 632, an antenna 634, and circuitry 636. The inward-facing light source 632 provides the emitted light 602 as described in FIG. 6A. The antenna 634 can be configured to send and/or receive the RF radiation 620 (shown in FIG. 6A) that pertains to communication between the external device 610 and the eye-mountable device 630 as described in relation to FIG. 6A. In some examples, circuitry 636 can be configured to determine modulation instructions to control the light source 632 based on the received RF signal 620. Circuitry 636 can also be configured to modulate the emitted light 602 by controlling the light source 632 such that the emitted light 602 is viewable through the pupil of the eye 10.

In some examples, the external device 610 can be configured to interrogate the eye-mountable device 630 via the RF radiation 620. The circuitry 636 included in the eye-mountable device 630 can be configured to receive instructions from the external reader 610 based on the RF radiation 620. For example, the circuitry 636 can be configured to obtain a reading from a sensor (not shown in FIG. 6B) included in the eye-mountable device 630 based on the received instructions. For example, the sensor can be configured to provide to the circuitry 636 the reading indicating biological vitals (e.g., blood pressure, heart rate, temperature, glucose level, psychological state, etc.) of a user of the eye-mountable device 630. The circuitry 636 can be configured to indicate the reading of the sensor to the external device 610 via the antenna 634 providing the RF radiation 620. The external reader 610 can receive the RF radiation 620 and display the biological vitals to the user via a display included in the reader (not shown in FIG. 6A).

In some examples similar to the previous example, the reading of the sensor may relate to an ambient environment of the user. For example, the reading may indicate humidity, temperature, ambient light intensity, etc. The external reader 610 can be configured to display information relating to the ambient environment to the user.

Figure 7:
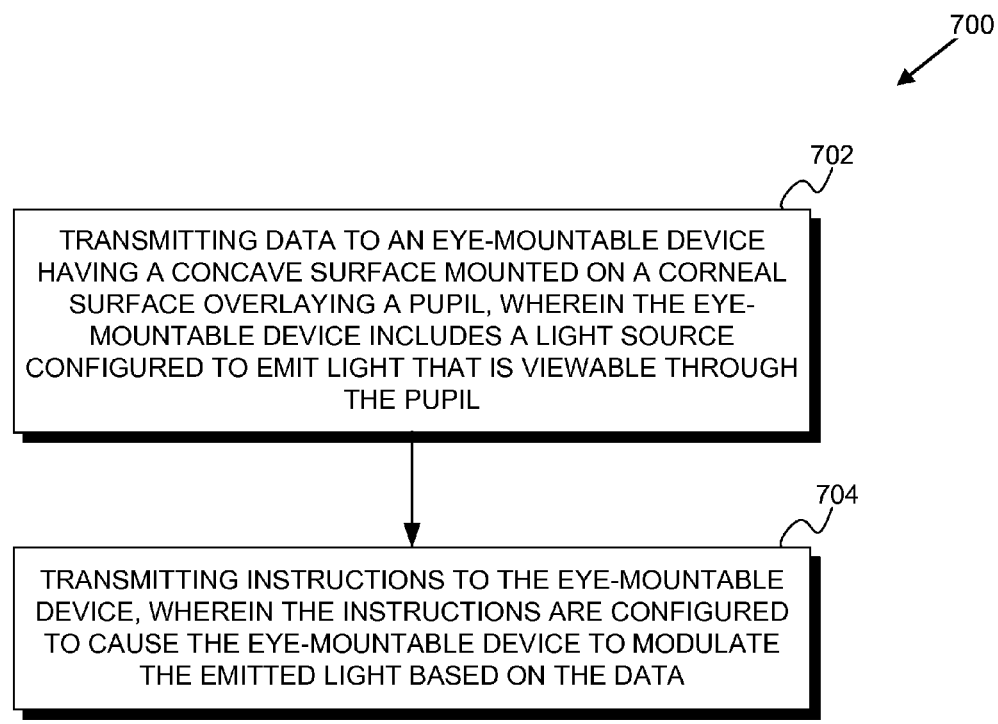
FIG. 7 is a block diagram of an example method 700 for operating an external device to operate an eye-mountable device, in accordance with at least some embodiments described herein.

FIG. 7 is a block diagram of an example method 700 for operating an external device to operate an eye-mountable device, in accordance with at least some embodiments described herein. Method 700 shown in FIG. 7 presents an embodiment of a method that could be used with the device 610, for example. Method 700 may include one or more operations, functions, or actions as illustrated by one or more of blocks 702-704. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 700 and other processes and methods disclosed herein, the flowchart shows functionality and operation of one possible implementation of present embodiments. In this regard, each block may represent a module, a segment, or a portion of a manufacturing or operation process.

At block 702, the method 700 includes transmitting data to an eye-mountable device having a concave surface mounted on a corneal surface overlaying a pupil, wherein the eye-mountable device includes a light source configured to emit light that is viewable through the pupil.

At block 704, the method 700 includes transmitting instructions to the eye-mountable device, wherein the instructions are configured to cause the eye-mountable device to modulate the emitted light based on the data.

For example, a computing device (e.g., smartphone, head-mounted device, etc.) can transmit data to an eye-mountable device indicative of a text message (step 702). The computing device can transmit instructions (step 704) on how to modulate light emitted by a light source included in the eye-mountable device to communicate the content of the text message using a code understandable to a user of the eye-mountable device (e.g., Morse code).

Figure 8:
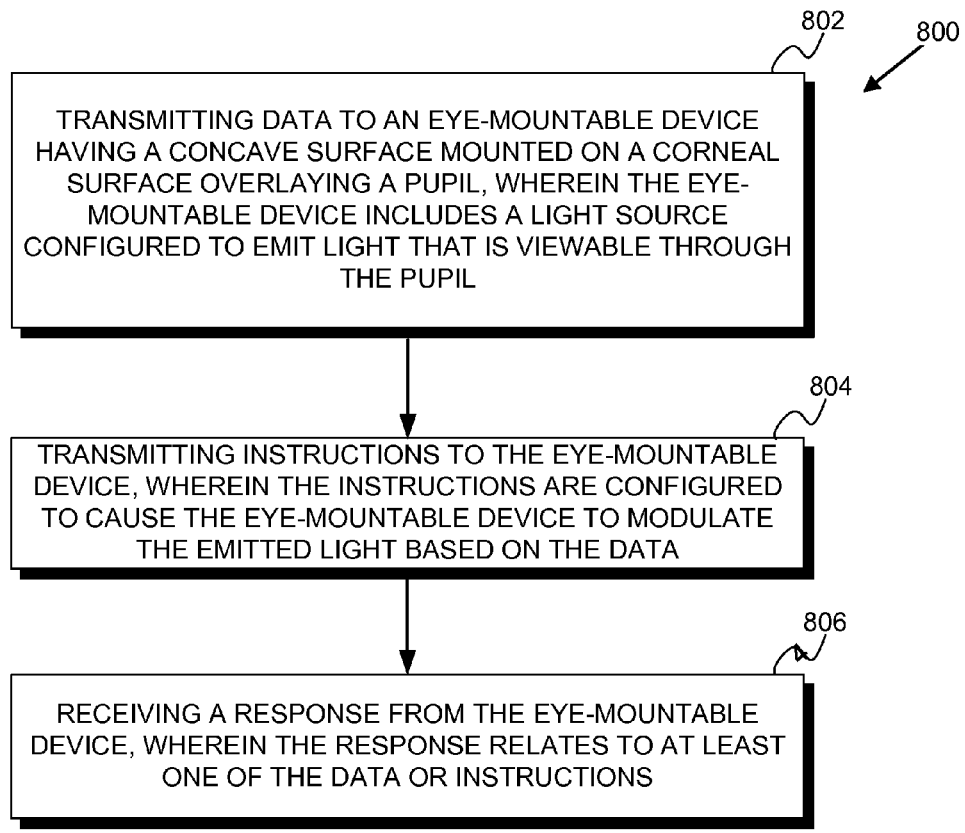
FIG. 8 is a block diagram of an example method 800 for operating an external device to communicate with an eye-mountable device, in accordance with at least some embodiments described herein.

FIG. 8 is a block diagram of an example method 800 for operating an external device to communicate with an eye-mountable device, in accordance with at least some embodiments described herein. Method 800 shown in FIG. 8 presents an embodiment of a method that could be used with the external device 610, for example. Method 800 may include one or more operations, functions, or actions as illustrated by one or more of blocks 802-806. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 800 and other processes and methods disclosed herein, the flowchart shows functionality and operation of one possible implementation of present embodiments. In this regard, each block may represent a module, a segment, or a portion of a manufacturing or operation process.

At block 802, the method 800 includes transmitting data to an eye-mountable device having a concave surface mounted on a corneal surface overlaying a pupil, wherein the eye-mountable device includes a light source configured to emit light that is viewable through the pupil.

At block 804, the method 800 includes transmitting instructions to the eye-mountable device, wherein the instructions are configured to cause the eye-mountable device to modulate the emitted light based on the data.

At block 806, the method 800 includes receiving a response from the eye-mountable device, wherein the response relates to at least one of the data or instructions.

For example, a computing device (e.g., smartphone) can include a global positioning system (GPS) sensor configured to provide a reading that pertains to a location of a user of an eye-mountable device. The reading of the GPS ("data") can be transmitted to the eye-mountable device wirelessly (Step 802). In addition, the user may select, via the computing device, a destination the user would like to navigate to. Thus, the computing device can transmit instructions to the eye-mountable device to cause the eye-mountable device to modulate the emitted light to guide the user (Step 804). For example, the eye-mountable device can modulate the emitted light to show a left arrow when the user is supposed to turn left and a right arrow when the user is supposed to turn right. The eye-mountable device can send a response to the computing device indicating that the eye-mountable device has completed modulating the emitted light (Step 806).

Figure 9:
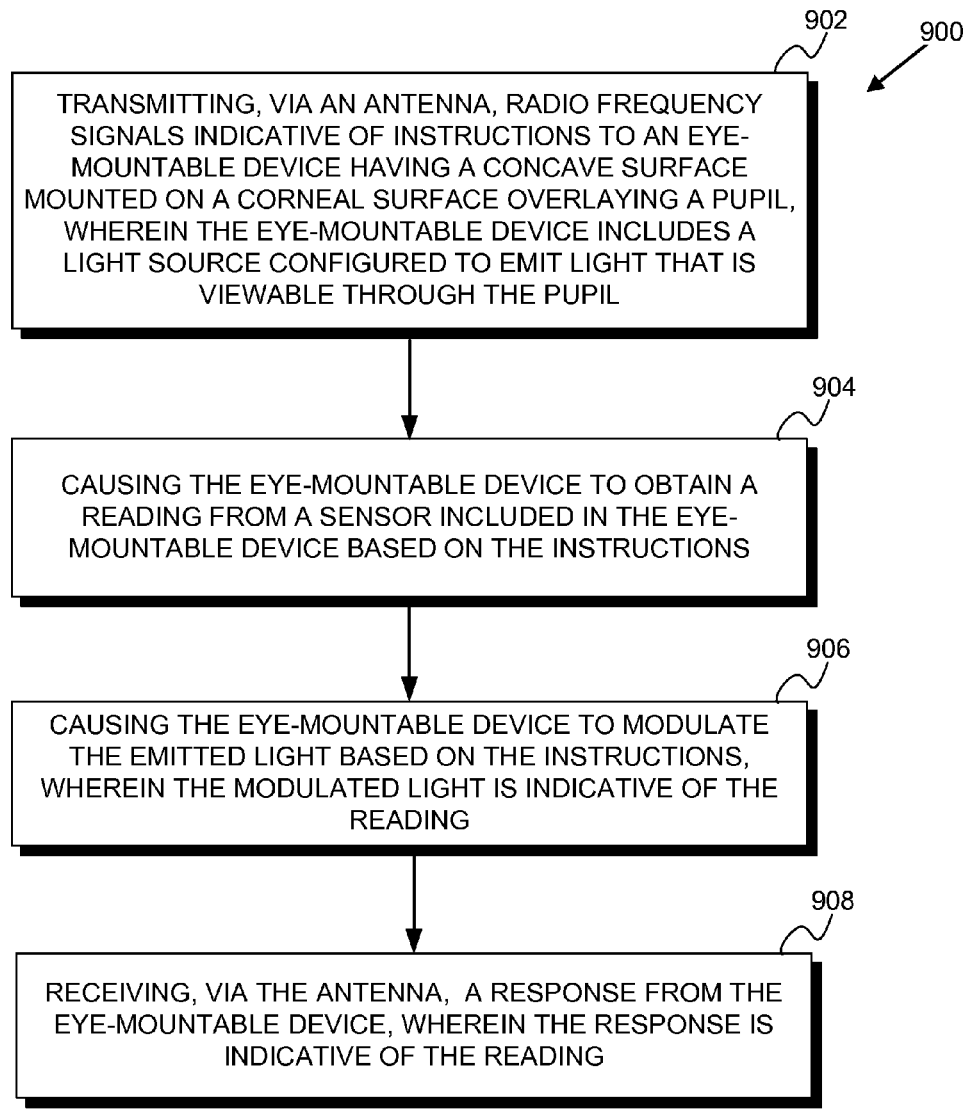
FIG. 9 is a block diagram of an example method 900 for operating an external device to communicate, via an antenna, with an eye-mountable device causing the eye-mountable device to obtain a reading of a sensor.

FIG. 9 is a block diagram of an example method 900 for operating an external device to communicate, via an antenna, with an eye-mountable device causing the eye-mountable device to obtain a reading of a sensor. Method 900 shown in FIG. 9 presents an embodiment of a method that could be used with the external device 610, for example. Method 900 may include one or more operations, functions, or actions as illustrated by one or more of blocks 902-908. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 900 and other processes and methods disclosed herein, the flowchart shows functionality and operation of one possible implementation of present embodiments. In this regard, each block may represent a module, a segment, or a portion of a manufacturing or operation process.

At block 902, the method 900 includes transmitting, via an antenna, radio frequency signals indicative of instructions to an eye-mountable device having a concave surface mounted on a corneal surface overlaying a pupil, wherein the eye-mountable device includes a light source configured to emit light that is viewable through the pupil.

At block 904, the method 900 includes causing the eye-mountable device to obtain a reading from a sensor included in the eye-mountable device based on the instructions.

At block 906, the method 900 includes causing the eye-mountable device to modulate the emitted light based on the instructions, wherein the modulated light is indicative of the reading.

At block 908, the method 900 includes receiving, via the antenna, a response from the eye-mountable device, wherein the response is indicative of the reading.

For example, a computing device (e.g., portable computer, smartphone, etc.) can be configured to transmit, via an antenna, radio frequency signals indicative of instructions to an eye-mountable device that includes a light source configured to emit light that is viewable through a pupil of an eye (Step 902). The eye-mountable device can include a glucose sensor that can measure glucose level in a tear film of the eye. The instructions can cause the eye-mountable device to obtain a reading of the glucose sensor (Step 904). The instructions can also cause the eye-mountable device to modulate light (step 906) emitted by a light source included in the eye-mountable device and viewable through a pupil of the eye indicating the reading of the sensor (e.g., red for high level, green for normal, blue for low, etc.). The eye-mountable device can also send a response to the computing device indicating a specific glucose level measurement for display on the computing device (Step 908).

Figure 10:
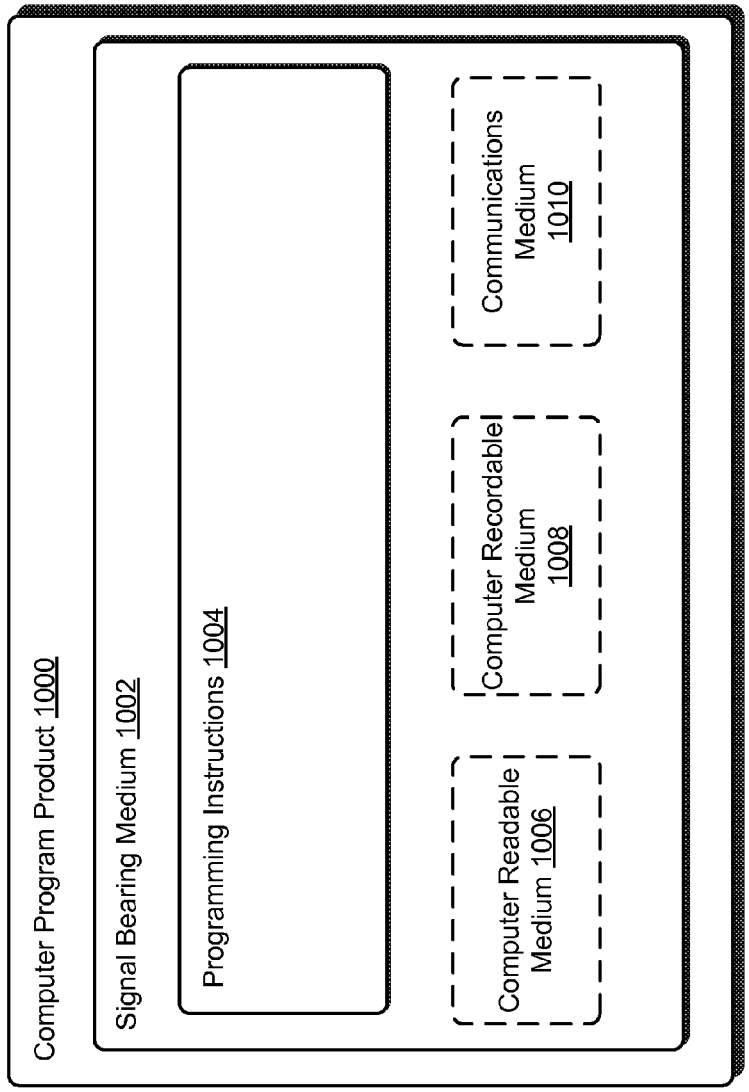
FIG. 10 depicts an example computer-readable medium configured according to at least some embodiments described herein.

FIG. 10 depicts an example computer-readable medium configured according to at least some embodiments described herein. In example embodiments, the example system can include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g. methods 300, 400, 500, 700, 800, and 900) can be implemented by computer program instructions encoded on a non-transitory computer readable storage media in a machine-readable format, or on other non-transitory media or articles of manufacture (e.g., the instructions stored on the memory 614 of the external device 610 of the system 600). FIG. 10 is a schematic illustrating a conceptual partial view of an example computer program product that includes a computer program for executing a computer process on a computing device, arranged according to at least some embodiments disclosed herein.

In one embodiment, the example computer program product 1000 is provided using a signal bearing medium 1002. The signal bearing medium 1002 may include one or more programming instructions 1004 that, when executed by one or more processors may provide functionality or portions of the functionality described above with respect to FIGS. 1-9. In some examples, the signal bearing medium 1002 can be a non-transitory computer-readable medium 1006, such as, but not limited to, a hard disk drive, a Compact Disc (CD), a Digital Video Disk (DVD), a digital tape, memory, etc. In some implementations, the signal bearing medium 1002 can be a computer recordable medium 1008, such as, but not limited to, memory, read/write (R/W) CDs, R/W DVDs, etc. In some implementations, the signal bearing medium 1002 can be a communication medium 1010 (e.g., a fiber optic cable, a waveguide, a wired communications link, a wireless communication link, etc.). Thus, for example, the signal bearing medium 1002 can be conveyed by a wireless form of the communications medium 1010.

The one or more programming instructions 1004 can be, for example, computer executable and/or logic implemented instructions. In some examples, a computing device such as the processor-equipped external device 610 of FIG. 6A is configured to provide various operations, functions, or actions in response to the programming instructions 1004 conveyed to the computing device by one or more of the computer readable medium 1006, the computer recordable medium 1008, and/or the communications medium 1010.

The non-transitory computer readable medium 1006 can also be distributed among multiple data storage elements, which could be remotely located from each other. The computing device that executes some or all of the stored instructions could be an external reader such as the external device 610 illustrated in FIG. 6A, or another mobile computing platform, such as a smartphone, tablet device, personal computer, head-mounted device, etc. Alternatively, the computing device that executes some or all of the stored instructions could be remotely located computer system, such as a server. For example, the computer program product 1000 can implement the functionalities discussed in the description of FIGS. 1-9.

Within examples, operation methods that are described for the device can be applied to other electronic devices that include an inward-facing light source. For example, eye implantable devices that measure biological information can include a light source directed inwards towards light sensing portions of the eye where the implantable devices are implanted. Thus, example methods herein provide operation methods that involve a device including an inward-facing light source, and modulating light emitted by the inward-facing light source such that the modulated light is viewable by a wearer of the device.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location) and an opportunity to control whether or how personal information is used. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and how the collected information is used.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. An eye-mountable device comprising:
a transparent material having a central region, a concave surface and a convex surface, wherein the concave surface is configured to be removably mounted on a corneal surface overlaying a pupil and the convex surface is configured to be compatible with eyelid motion when the concave surface is mounted on the corneal surface;
a ring-shaped substrate at least partially embedded in the transparent material;
a light source disposed on the ring-shaped substrate away from the central region of the transparent material, wherein the light source is configured to emit light that is viewable through the pupil when the concave surface is mounted on the corneal surface; and
circuitry disposed on the ring-shaped substrate, wherein the circuitry is configured to modulate the light emitted by the light source to provide modulated light.

2. The eye-mountable device of claim 1, wherein the circuitry is configured to modulate at least one of a color, brightness, intensity, or duration of the light emitted by the light source.

3. The eye-mountable of claim 1, further comprising a photovoltaic cell, wherein the photovoltaic cell is configured to provide power to the eye-mountable device based on light incident on the photovoltaic cell.

4. The eye-mountable device of claim 1, further comprising an optical element optically coupled to the light source, wherein the optical element is configured to focus the light emitted by the light source through the pupil.

5. The eye-mountable device of claim 4, wherein the optical element comprises a Fresnel lens.

6. The eye-mountable device of claim 1, wherein the modulated light is indicative of a message.

7. The eye-mountable device of claim 6, wherein the message relates to a status of the eye-mountable device or a status of components included in the eye-mountable device.

8. The eye-mountable device of claim 6, further comprising a sensor disposed on the ring-shaped substrate and coupled to the circuitry, wherein the sensor is configured to obtain a reading, and wherein the message relates to the reading.

9. The eye-mountable device of claim 6, further comprising an antenna disposed on the ring-shaped substrate and coupled to the circuitry, wherein the antenna is configured to receive information, and wherein the message relates to the received information.

10. The eye-mountable device of claim 9, wherein the antenna is configured to provide power to the eye-mountable device based on radiation incident on the antenna.

11. The eye-mountable device of claim 9, wherein the antenna is configured to transmit information indicative of a status of the eye-mountable device or a status of components included in the eye-mountable device.

12. The eye-mountable device of claim 1, wherein the ring-shaped substrate has a first side facing the concave surface and a second side facing the convex surface.

13. The eye-mountable device of claim 12, wherein the light source and circuitry are disposed on the first side of the ring-shaped substrate.

14. The eye-mountable device of claim 13, further comprising a loop antenna disposed on the first side of the ring-shaped substrate.

15. The eye-mountable device of claim 14, wherein the loop antenna extends around the first side of the ring-shaped substrate except for a cutout area, and wherein the light source and circuitry are disposed in the cutout area.

16. The eye-mountable device of claim 1, further comprising an optical element, wherein the optical element is configured to receive light emitted from the light source at an oblique angle and to direct the emitted light so as to be viewable through the pupil.

* * * * *